United States Patent [19]

Schmid

[11] Patent Number: 4,700,712

[45] Date of Patent: Oct. 20, 1987

[54] METHOD FOR DETERMINING THE STARTING POINT AND THE END POINT OF CLOSED SPATIAL SIGNAL PATTERNS

[75] Inventor: Johann J. Schmid, Buchs, Switzerland

[73] Assignee: Willi Studer AG, Regensdorf, Switzerland

[21] Appl. No.: 896,835

[22] Filed: Aug. 15, 1986

[30] Foreign Application Priority Data

Aug. 30, 1985 [CH] Switzerland ............... 03734/85

[51] Int. Cl.$^4$ .................. A61B 5/04; G06F 15/42; G06G 7/60
[52] U.S. Cl. ................... 128/699; 364/417
[58] Field of Search ............. 128/699; 364/417

[56] References Cited

U.S. PATENT DOCUMENTS

| | | | |
|---|---|---|---|
| 3,884,221 | 5/1975 | Eastman | 128/699 |
| 4,085,407 | 4/1978 | Stratbucker et al. | 128/699 |
| 4,136,690 | 1/1979 | Anderson et al. | 128/699 |
| 4,587,976 | 5/1986 | Schmid | 128/699 |
| 4,616,333 | 10/1986 | Shimoni | 364/417 |

Primary Examiner—William E. Kamm
Assistant Examiner—Timothy Keegan

[57] ABSTRACT

The spatial closed signal pattern is represented by measured signals picked up from a living being by means of electrodes. Sequences of consecutive spatial slope values are formed for each spatial closed signal pattern and different such sequences associated with different spatial closed signal patterns are mutually correlated. As a result of such correlation, the sequences are classified according to different classes and there is determined a temporal offset between such sequences. Minimum spatial slope values respectively associated with the starting region and the end region of each sequence are determined for each class. Predetermined time intervals about the moments of time which are associated with such minimum spatial slope values, are investigated for those sampling moments of time associated with the measured data having the smallest mutual spatial distance. The moments of time at which these measured data appear, constitute the starting point and the end point of the related spatial closed signal pattern.

8 Claims, 10 Drawing Figures

METHOD FOR DETERMINING THE STARTING POINT AND THE END POINT OF CLOSED SPATIAL SIGNAL PATTERNS

CROSS-REFERENCE TO RELATED PATENT

This application is related to the commonly assigned U.S. Pat. No. 4,587,976, granted May 13, 1986, and entitled "METHOD OF, AND APPARATUS FOR, DETERMINING THE STARTING POINT AND THE END POINT OF CLOSED SIGNAL PATTERNS", the disclosure of which is incorporated herein by reference.

BACKGROUND OF THE INVENTION

The present invention relates to a new and improved method of determining the starting point and the end point of a spatial closed signal pattern in a time sequence of individual ones of such spatial closed signal patterns, each of which is constituted by a series of measuring signals, which are picked up by means of electrodes from a living being.

During a method as known, for example, from European Patent Publication No. 0,150,352 cognate with the aforementioned U.S. Pat. No. 4,587,976 and which method is particularly intended for determining the starting point and the end point of a QRS loop or wave within a vector cardiogram curve, there are defined in a first step, two time intervals for such QRS loop or wave. These time intervals are in correspondence with related sections of projections of vectorial representations of the QRS loop or wave onto predetermined planes of, for example, a triaxial coordinate system. The two points of such sections and which points have the shortest spatial distance with respect to each other, are designated as the zero points of the QRS loop or wave. The two points correspond to the starting point and the end point of the QRS loop or wave.

Using this previously known method it is possible to determine with high precision the starting points and the end points of the QRS loops or waves in vector cardiogram curves. However, this method requires relatively high computation expenditure because there must be determined the spatial distances between a relatively large number of sampled values of the digitized measured signals. Although high-capacity computers are capable of handling these computations efficiently, it is desirable to reduce the necessary computation expenditure.

SUMMARY OF THE INVENTION

Therefore, with the foregoing in mind it is a primary object of the present invention to provide a new and improved method of determining the starting point and the end point of a spatial closed signal pattern in a time sequence of individual ones of such spatial closed signal patterns, each of which is constituted by a series of measured signals, in a manner which is not afflicted with the aforementioned drawbacks and limitations of the hitherto known methods.

Another important object of the present invention is directed to providing a new and improved method of determining the starting point and the end point of a spatial closed signal pattern in a time sequence of individual ones of such spatial closed signal patterns, each of which is constituted by a series of measured signals, and which method requires comparatively small computation expenditure and yet ensures highly reliable determination of the starting point and the end point of such spatial closed signal pattern.

Now in order to implement these and still further objects of the invention, which will become more readily apparent as the description proceeds, the method of the present development is manifested by the features that, there is determined a predetermined number of spatial slope values of the spatial closed signal patterns. There are then selected sequences of consecutive spatial slope values from the different spatial closed signal patterns, and the consecutive spatial slope values of these sequences are mutually correlated. As a result of such correlation, the sequences are associated with different classes and there is formed from the aforementioned sequences for each such class a sequence of consecutive weighted average spatial slope values. As a further result of the correlation there is determined for each sequence a temporal offset with respect to the sequence of consecutive weighted average spatial slope values. A minimum spatial slope value is determined for each end region of the sequence of consecutive weighted average spatial slope values. Subsequently there are determined, from the minimum spatial slope values of the sequence of consecutive weighted average spatial slope values and the temporal offset, a moment of time associated with the minimum spatial slope values of each individual sequence of consecutive spatial slope values. These moments of time are respectively defined as the starting point and the end point of each individual sequence of consecutive spatial slope values, i.e. each individual spatial closed signal pattern from which such sequence of consecutive spatial slope values was originally derived.

It is one important advantage of the inventive method that the computational expenditure is significantly reduced. Thus, the minimum spatial distance between the measured values or data of each spatial closed signal pattern is formed from a substantially smaller number of measured values or data because the environment of such starting point or end point is already more accurately known. As a further result there is obtained higher reliability regarding the determination of the true starting point and the true end point.

The inventive method further permits ready determination of the known J-point which is defined as the first spatial slope value at the end of a QRS loop or wave which is below a predetermined limit. In healthy human beings this J-point coincides with the end point of the QRS loop or wave.

The inventive method furthermore permits classification of the individual detected spatial closed signal patterns and thereby facilitates determining the significance of individual ones of the spatial closed signal patterns.

BRIEF DESCRIPTION OF THE DRAWINGS

The invention will be better understood and objects other than those set forth above, will become apparent when consideration is given to the following detailed description thereof. Such description makes reference to the annexed drawings wherein throughout the various figures of the drawings there have been generally used the same reference characters to denote the same or analogous components and wherein.

DETAILED DESCRIPTION OF THE PREFERRED EMBODIMENTS

Describing now the drawings, it is to be understood that only enough of the method has been illustrated as needed for those skilled in the art to readily understand the underlying principles and concepts of the present development, while simplifying the showing of the drawings. Turning attention now specifically to FIG. 1, there has been shown as an example of a physiological measuring signal a section of a vector cardiogram curve 1. Therein electrode potential values which are picked up from an investigated person or patient by means of electrodes, are plotted on a time axis 2. Since the inventive method will be explained with reference to the example of a vector which represents the heart action of a living being and which continuously changes its magnitude and direction as a function of time, the potential values illustrated in FIG. 1 can be considered as the magnitude of the vector projected into a predetermined plane.

Figure 1:
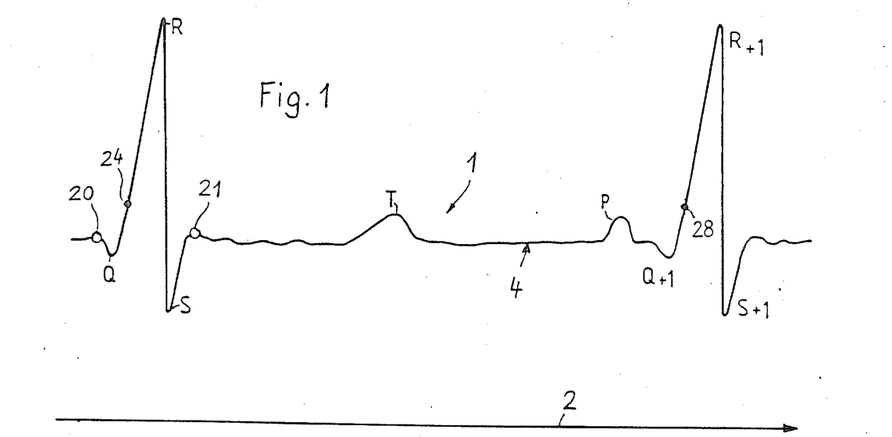
FIG. 1 is an illustration in a predetermined plane along a time axis of a physiological measured signal which is picked up from a person or patient under investigation by means of electrodes.

Such a vector or the potential values associated with its tip or end point describes a time sequence of consecutive signal or electrode potential patterns, each of which is described by the cardiologist as comprising a QRS loop or wave, a T-loop or wave and a P-loop or wave. Sections 4 are interposed intermediate these loops or waves in curve 1 and these sections 4 are rather short and more or less indicate constant potential values.

Figure 2:
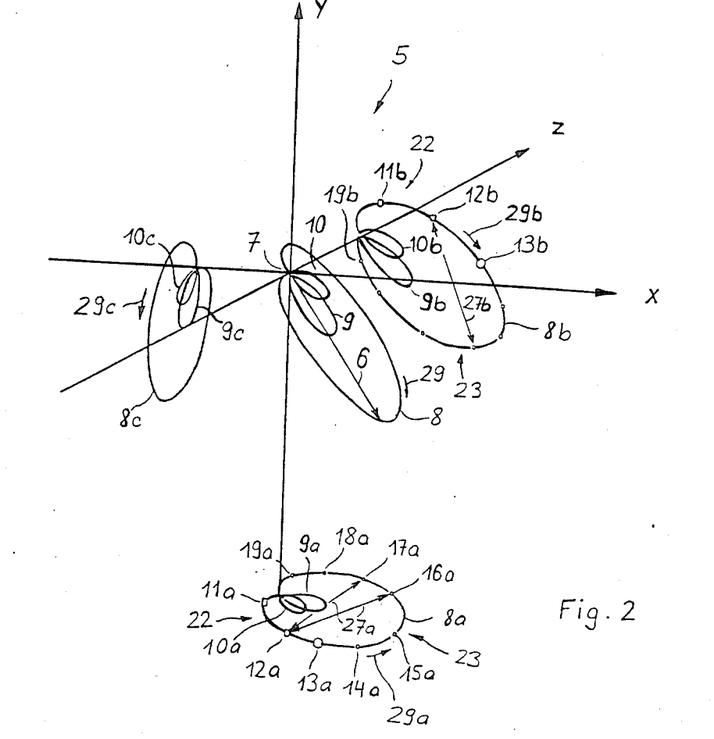
FIG. 2 is an illustration of the measured signal shown in FIG. 1 and shows one spatial closed signal pattern in space as well as in projection onto three different planes.

FIG. 2 shows the vector 6 in a triaxial coordinate system 5 defining an orthogonal or rectangular coordinate system and illustrates the vector 6 at a specific moment of time by means of an arrow. This vector 6 starts from a null or zero point 7 and ends at points in space which together form the loops or waves 8, 9 and 10. The loop 8 of such vectorial illustration is also designated as QRS loop, the loop 9 as T-loop and the loop 10 as P-loop. By means of the X, Y and Z axes of the coordinate system 5 an XY plane, an XZ plane and a YZ plane are defined. The loops 8, 9 and 10 can be projected onto these three planes such that further loops 8a, 8b, 8c; 9a, 9b, 9c; and 10a, 10b, 10c can be recognized. In order to facilitate the following explanations there are also entered individual points 11a to 19a and 11b to 19b along the loops 8a and 8b, respectively.

FIGS. 3a, 3b, 3c and 3d illustrate a continuous flow diagram containing brief and illustrative descriptions of the steps of the inventive method. These individual steps are designated by reference characters 31 to 54. The flow diagram is believed to be self-explanatory and, therefore, will not be described in further detail at this place. However, reference will be made to this flow diagram hereinafter in the description of the mode of operation of the inventive method.

Figure 4:
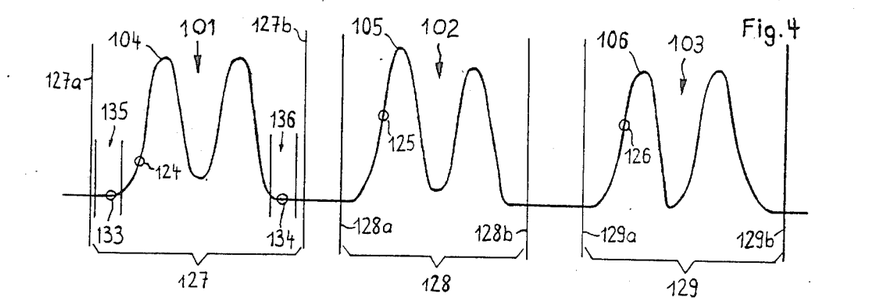
FIG. 4 is a diagram showing the time variation of the spatial slope of three individual QRS loops or waves in three individual spatial closed signal patterns shown in FIG. 2 but in a simplified illustration for ease of understanding.

FIG. 4 illustrates, for example, with reference to three consecutive heart cycles or beats 101, 102 and 103 spatial slope signals 104, 105 and 106 which show the time variation of the spatial slope values of the vector 6 in the QRS loops or waves 8 during each one of the heart cycles or beats 101, 102 and 103 in a simplified representation. The T-loops or waves 9 as well as the P-loops or waves 10 have been omitted from the illustration in FIG. 4.

Figure 5:
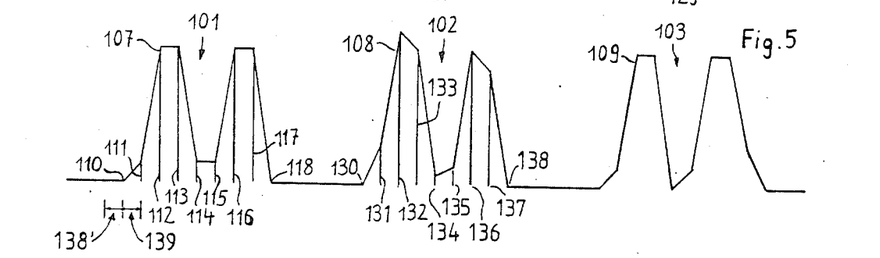
FIG. 5 is a schematic diagram showing three sequences of consecutive spatial slope values derived from the spatial slope as a function of time signals of the three QRS loops or waves illustrated in FIG. 4.

FIG. 5 shows, for the same heart cycles or beats 101, 102 and 103 referred to in FIG. 4, graphically simplified spatial slope signals or sequences 107, 108 and 109 of consecutive spatial slope values. These simplified spatial slope signals or sequences 107, 108 and 109 correspond to the spatial slope signals 104, 105 and 106 and are derived therefrom; they are illustrated in order to simplify the explanations given hereinbelow. While illustrated only schematically for the sequences 107 and 108, it is true for all of the spatial slope signals 104 to 109, that these signals are composed of sequences of consecutive spatial slope values which are associated with the vector 6 and determined from digital scanning or sampling values of the related QRS loops or waves 8. Individual such digitally determined or detected spatial slope values are specifically indicated by reference numerals 110 to 118 in the sequence 107 and by the reference numerals 130 to 138 in the sequence 108.

Figure 6:
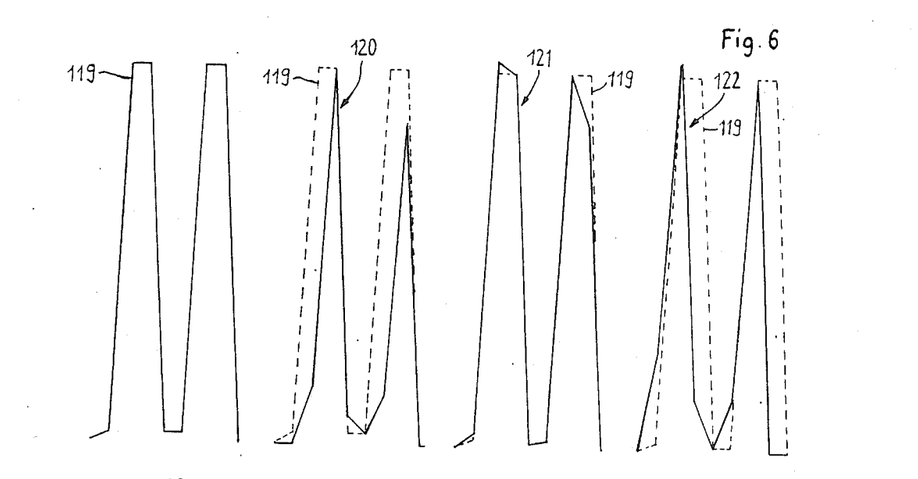
FIG. 6 is a schematic illustration of a modified representation of the first sequence of consecutive spatial slope values shown in FIG. 5 and its correlation patterns obtained by correlating such first sequence of consecutive spatial slope values with the second sequence of consecutive spatial slope values shown in FIG. 5.

FIG. 6 shows a further spatial slope signal 119 which is composed of a sequence of products derived from the consecutive spatial slope values of the sequence 107 shown in FIG. 5. In order to obtain the further spatial slope signal 119, each one of the spatial slope values 110 to 118 in the sequence 107 is multiplied by itself or squared and placed at the same location, i.e. plotted at the same moment of time at which the consecutive spatial slope values 110 to 118 are plotted in the sequence 107 in FIG. 5. By multiplying the consecutive spatial slope values of the sequence 107 in FIG. 5 with the consecutive spatial slope values 130 to 137 in the sequence 108 in FIG. 5 there are obtained the further spatial slope signals 120, 121 and 122. Specifically, the signals 120 and 122 are obtained by multiplication at a predetermined temporal offset between the sequence 107 and the sequence 108.

In the illustrated embodiment the temporal offset amounts to one scanning or sampling interval. Specifically, the further spatial slope signal 120 is obtained by temporally offsetting the sequence 107 relative to the sequence 108 by one scanning or sampling interval 138' to an earlier moment of time such that there are multiplied the spatial slope values 111 and 130, 112 and 131, etc. In analogous manner, the further spatial slope signal 122 is obtained by temporally offsetting the sequence 107 relative to the sequence 108 by one scanning interval 139 to a later moment of time such that there are multiplied the spatial slope values 110 and 131, 111 and 132, etc. The further spatial slope signal 121 is obtained at no temporal offset between the sequence 107 relative to the sequence 108.

Figure 7:
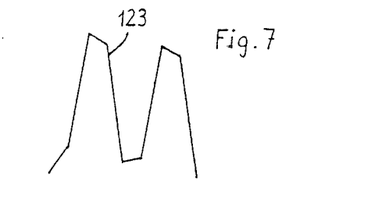
FIG. 7 is a graphic representation of a sequence of consecutive weighted average spatial slope values obtained as the result of mutually correlating the first sequence of consecutive spatial slope values and the second sequence of consecutive spatial slope values shown in FIG. 5.

FIG. 7 shows a correlation signal or sequence 123 of consecutive weighted average spatial slope values obtained by the aforedescribed weighted averaging between the sequences 107 and 108.

In the following there will now be described the individual steps of the inventive method which permits determining the starting point and the end point of recurring individual spatial closed signal or electrode potential patterns, specifically of, for example, a QRS loop in a vector cardiogram. Since the vector in each such vector cardiogram successively describes a QRS loop, a T loop and a P loop, it is important to know, for example, at which point and at which time the QRS loop starts and ends because the QRS loop gives the physician an indication with respect to certain aspects of the cardiac action while the T loop or the P loop give indications with respect to other aspects of the cardiac action.

In order to obtain reliable data about the position of the starting point 20 and the end point 21 of the QRS wave or loop, see FIG. 1, it is essential to detect the movements of the vector 6 and thus the QRS loop 8, in different planes. Therefore, during the preparation of a vector cardiogram, there are periodically or continuously detected in a manner which is known as such, the values of the electrode potential which is represented by the vector 6. The graphic illustration of such electrode potential values, when plotted in a predetermined plane along the time axis 2, results in the curve 1 shown in FIG. 1. The graphic illustration of such potential values, when plotted in the XZ plane, in the XY plane, and in the ZY plane, i.e. in the triaxial coordinate system 5, results in the respective QRS loops 8a, 8b, and 8c.

During non-continuous digital detection of the electrode potential values, X-values, Y-values and Z-values of the electrode potential are determined and stored at predetermined scanning or sampling moments of time or intervals. During this operation the incoming analog values of the electrode potential are quantized in known fashion after prior filtering and converted into digital values. This corresponds to the step 31 shown in FIG. 3a. A suitable combination of such values obtained along two different axes of the triaxial coordinate system 5 produces the points 11a to 19a of the QRS loop 8a or, for example, points 11b to 19b of the QRS loop 8b. In each such combination the potential values which are associated with analogous points, have been detected at the same scanning or sampling moment of time.

In accordance with step 32 shown in FIG. 3a, there is subsequently computed a spatial slope value of the vector 6 from the difference between the potential values which have been detected at two consecutive scanning or sampling moments of time. The computation of the spatial slope value is based on the following formula:

$$f(x,y,z,t) =$$

-continued $$\sqrt{[x(t + T) - x(t)]^2 + [y(t + T) - y(t)]^2 + [z(t + T) - z(t)]^2}$$

This operation can be carried out separately for each plane of the coordinate system 5. As an example, there are determined slope values for the region between the points 12a and 13a in the XZ plane of projection, the points 12b and 12c in the XY plane or projection, etc. The operation is carried out on all scanned or sampled potential values of the QRS loops 8a, 8b and 8c, and there are obtained three slope values for each region between two consecutive points in the three XZ, XY and ZY planes. These slope values are fed to a bandpass filter so that extreme slope values are eliminated, see step 32a in FIG. 3a. There is then computed from all of the thus obtained slope values the spatial slope value in accordance with the formula given hereinbefore. An average spatial slope value is computed from all of the thus obtained spatial slope values as provided in step 33 of FIG. 3a.

Figure 3A:
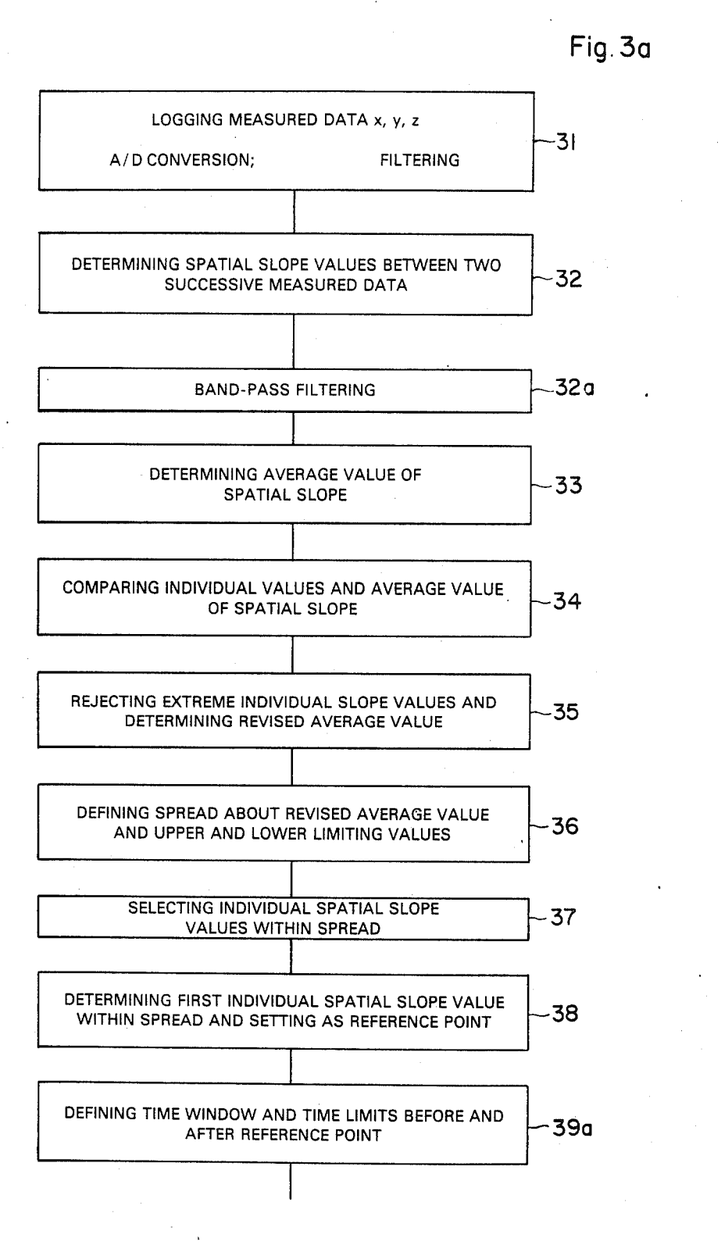
FIGS. 3a, 3b, 3c, and 3d collectively represent a flow diagram or chart illustrating the steps of the inventive method.

By comparing the individual spatial slope values with the average spatial slope value, see step 34 in FIG. 3a, it is possible, for example, to eliminate spatial slope values which deviate by a predetermined amount from the average spatial slope value, and to disregard such unacceptably deviating spatial slope values during the further procedure. A revised average spatial slope value is then computed during step 35 in FIG. 3a from the remaining spatial slope values.

A predetermined spread or band width is defined with respect to the revised average spatial slope value and selected such that the spatial slope values of the vector 6 can be reasonably expected to fall within such spread or band width. This is carried out in step 36 shown in FIG. 3a. This step is provided, for example, in order to exclude from consideration extrasystoles which may occur during the heart cycle or beat and which are associated with very high spatial slopes. This spread or band width is limited by an upper limiting value and a lower limiting value for the spatial slope.

Subsequently, and during step 37, there are selected those spatial slope values which fall within the predetermined spread or band width and therefrom, during step 38, a first spatial slope value which is associated with a sequence of consecutive spatial slope values of the same direction. These first spatial slope values within the predetermined spread or band width are designated as trigger or reference times or points, see reference characters 124, 125, 126 in FIG. 4, and stored for each one of the spatial slope signals 104, 105 and 106. Each QRS loop or wave 8 and its associated sequence of consecutive spatial slope values thus is provided with a reference time or reference moment of time designated by the reference character 24 in FIG. 1. For the following discussion there is essential only a moment of time which precedes such reference time or reference moment of time 24.

Related time windows 127, 128, 129, see FIG. 4, are then set or defined for each one of the trigger or reference times or points 124, 125 and 126 in step 39a. Each time window 127, 128, 129 is limited by related time limits 127a, 128a, 129a preceding the reference time or point 124, 125 or 126, as the case may be, and by related time limits 127b, 128b, 129b following such reference time or point. The time windows 127, 128, 129 are selected sufficiently wide to accommodate the spatial slope values associated with the related QRS loop or wave 8.

Figure 3B:
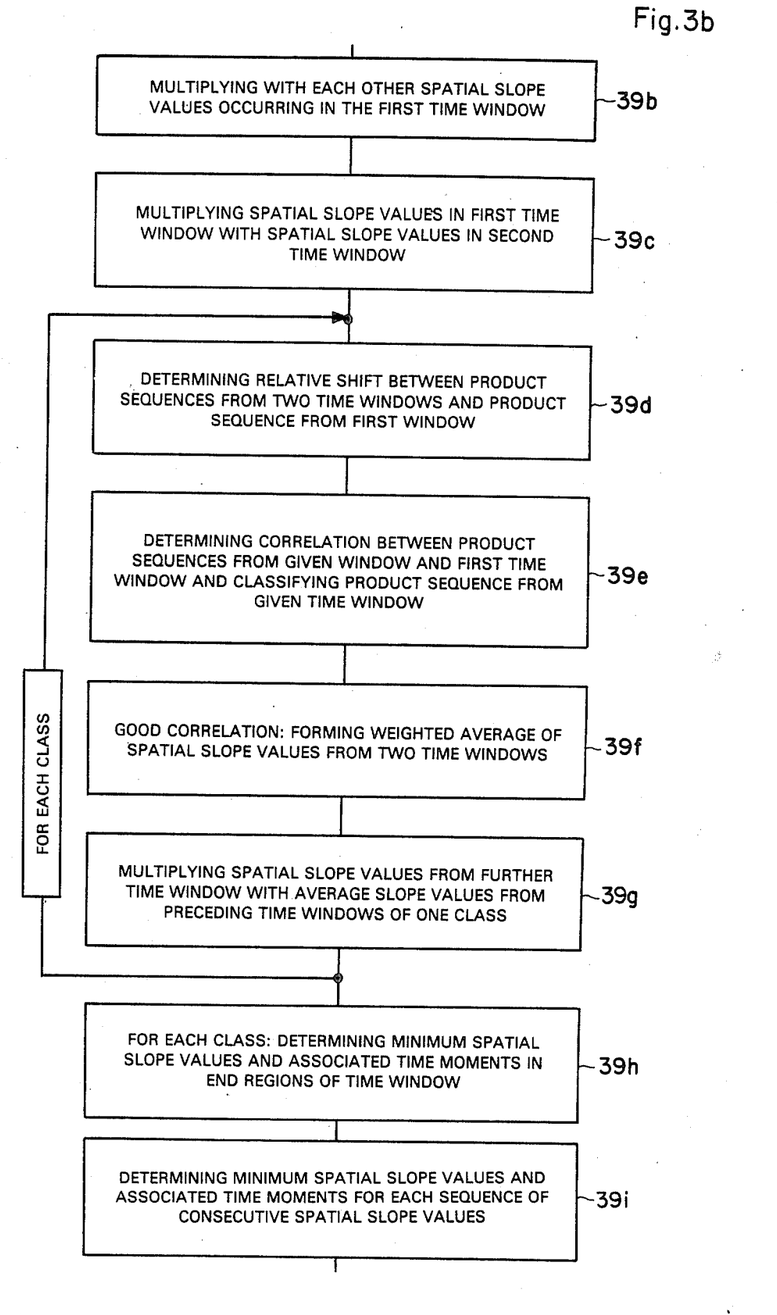
Figure 3C:
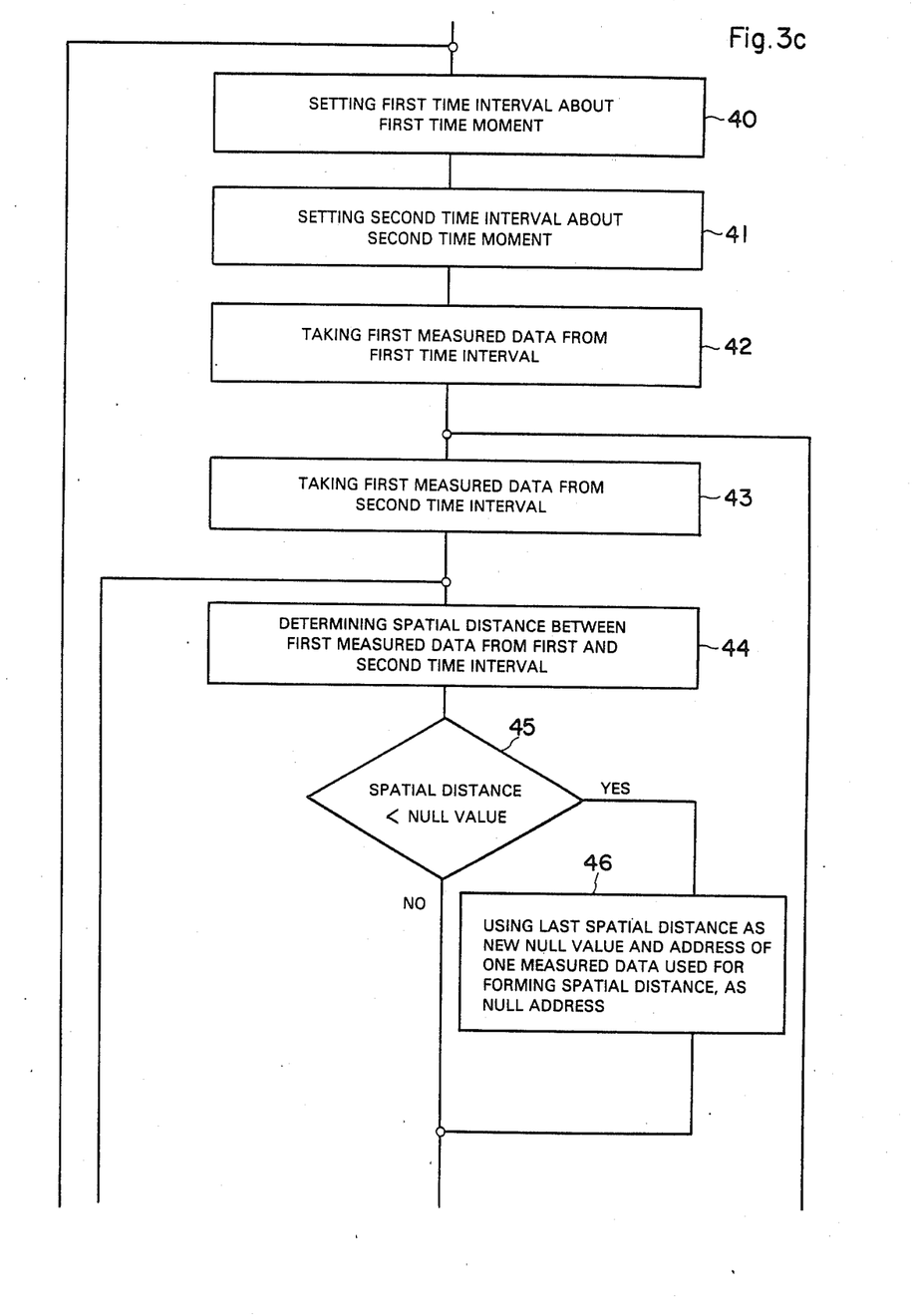
Figure 3D:
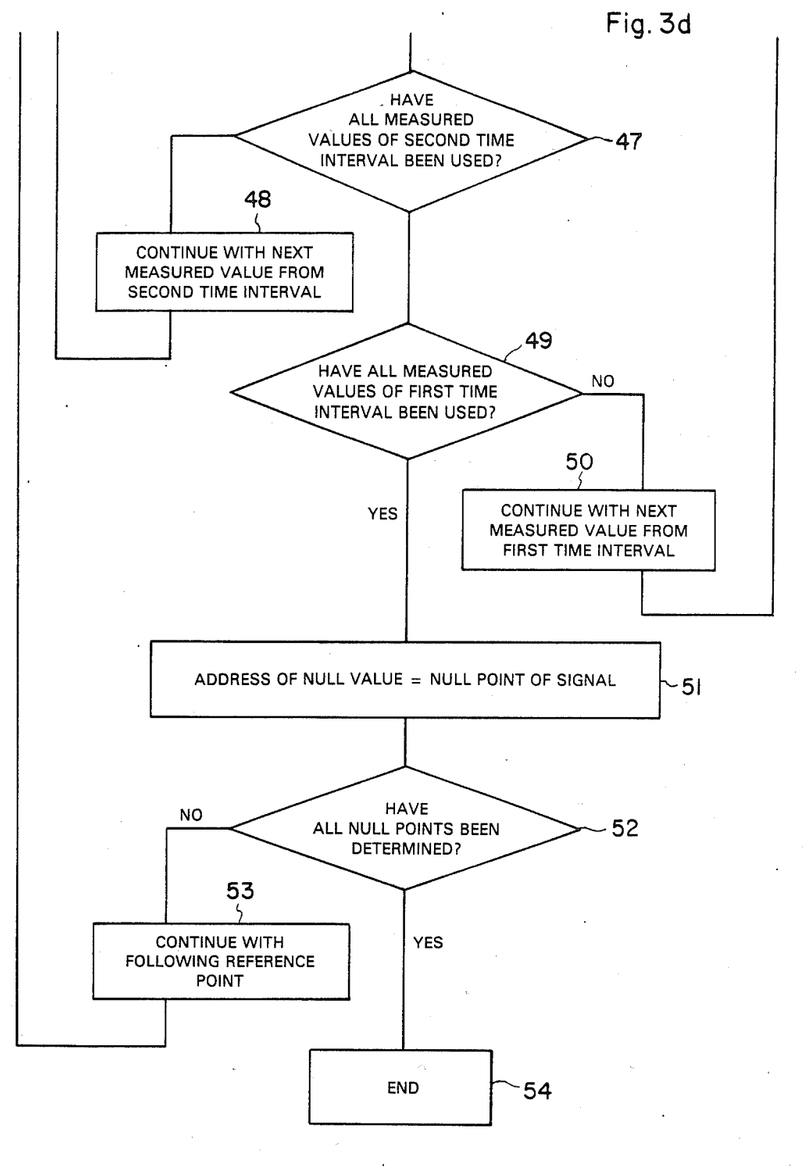

During step 39b, see FIG. 3b, spatial slope values associated with predetermined scanning or sampling moments of time within the first time window 127 of a group of several time windows 127, 128, 129, etc. and which time window 127 also is associated with the spatial slope signal 104 which, in turn, is associated with the heart cycle or beat 101, are multiplied by themselves or squared. Since each time window 127, 128, 129, etc. comprises an equal number of scanning or sampling moments of time, this step 39b is only concerned with multiplying by itself or squaring those spatial slope values of the sequence of consecutive spatial slope values which belong to the same time window 127, 128, 129, etc. and the same reference time or point 124, 125, 126, etc., as the case may be, and which are associated with the same scanning or sampling moments of time within each such time window 127, 128, 129, etc. prior to each time limit 127b, 128b, 129b, etc. thereof. From, for example, 100 spatial slope values, there are thus formed 100 products or squares of such spatial slope values. Considering FIG. 5 and therein the sequence 107 of consecutive spatial slope values 110 to 118, these consecutive spatial slope values 110 to 118 occur within the time window 127 at predetermined scanning or sampling moments of time preceding the limiting time 127b. As a result of the multiplying or squaring operation, there is obtained the further spatial slope signal 119 shown in FIG. 6.

According to the subsequent step 39c in FIG. 3b, the consecutive spatial slope values 110 to 118 associated with the first time window 127 are multiplied with the consecutive spatial slope values 130 to 138 associated with the second time window 128. In the simplified illustration of FIG. 5, this implies that the spatial slope value 110 is multiplied with the spatial slope value 130, the spatial slope value 111 is multiplied with the spatial slope value 131, the spatial slope value 112 is multiplied with the spatial slope value 132, etc. These multiplications of the consecutive spatial slope values which are respectively associated with the first and second time windows 127 and 128, are carried out such that the multiplications are different with respect to the time sequences of consecutive spatial slope values which are used for the multiplication from one or the other of the two time windows 127 or 128. For instance, there are respectively used from the sequence 107, sequences of consecutive spatial slope values which start at the scanned or sampled spatial slope value 111, at the scanned or sampled spatial slope value 112, or even at a scanned or sampled spatial slope value which precedes the scanned or sampled spatial slope value 110. Consequently, during the aforementioned multiplications, one of the two sequences of consecutive spatial slope values is offset relative to the other sequence by one or more scanning or sampling moments of time or scanning or sampling intervals 138′, 139.

As a result of such multiplications of the sequence 107 of consecutive spatial slope values 110 to 118 with the sequence 108 of consecutive spatial slope values 130 to 138 there are obtained the further spatial slope signals 120, 121 and 122 shown in FIG. 6 at different displacements or offsets up to two scanning or sampling intervals. As an example, the further spatial slope signal 120 is produced by advancing the sequence 107 by one scanning or sampling interval 138 and the further spatial slope signal 122 is produced by rearwardly offsetting the sequence 107 by one sampling interval 139.

During correlation of the product sequences obtained in step 39c and the product sequence obtained in step 39b, the product sequences which represent the further spatial slope signals 120, 121, 122, etc., are compared with the further spatial slope signal 119 or the related product sequence. Each further spatial slope signal 120, 121, 122, etc., is associated with a value for the temporal offset which was used during its generation. By this comparison there is determined which product sequence or which further spatial slope signal 120, 121, 122 is in optimum conformity with the further spatial slope signal 119 or its product sequence as well as the extent of the occurring deviations. This procedure is generally known as a correlation operation and is carried out in steps 39d and 39e. As a result of such correlation there are obtained data indicating which of the product sequences obtained by multiplying the consecutive spatial slope values in two time windows, most closely conforms with the sequence of consecutive spatial slope value products obtained from the first time window alone. Such data also indicate the number of scanning or sampling intervals 138′, 139 by which one of the sequence of consecutive spatial slope values has been offset relative to the other during multiplication.

Furthermore, there is determined a correlation factor for that product sequence obtained from the consecutive spatial slope values in the first and second time window which is in optimum conformity with the product sequence obtained from the consecutive spatial slope values of the first time window alone. Such correlation factor is indicative of the degree of correlation or conformity which exists between the different product sequences. Product sequences of poor conformity can be recognized by their correlation factor and are eliminated or assigned to a different correlation class, where they can be investigated separately. It is also possible to define the various correlation classes in advance and to continuously associate the product sequences with the different correlation classes according to their degree of conformity or correlation.

For two product sequences obtained from consecutive spatial slope values of two consecutive time windows like, for example, the first time window 127 and the second time window 128, provided there exists good correlation between the two product sequences, there is produced in step 39f a sequence of consecutive weighted average spatial slope values and such sequence is represented by the correlation signal 123 shown in FIG. 7.

Thereafter, the sequence of consecutive weighted average spatial slope values is multiplied in the aforedescribed manner with the corresponding sequence of consecutive spatial slope values associated with a further time window, i.e., the sequence 109 in the third time window 129. There is thus obtained in essentially analogous manner and by also utilizing predetermined temporal offset, a number of the aforedescribed product sequences of consecutive spatial slope values, see step 39g of FIG. 3a. Subsequently, the steps 39d, 39e, 39f, and 39g are repeated, first for product sequences of the same correlation class and then for product sequences of the other correlation classes.

After all of the sequences of consecutive spatial slope values of all time windows 127, 128, 129, etc. have been processed in accordance with the method described hereinbefore, there are obtained different correlation classes for the sequences of products of consecutive spatial slope values and each correlation class contains such product sequences. There is associated with each correlation class a sequence of consecutive weighted average spatial slope values. In addition, each correlation class also contains the individual sequences of consecutive spatial slope values which are associated with a specific time window. All these values are stored in an appropriately selected memory or storage device.

During step 39h in FIG. 3b, there is now investigated each sequence of the consecutive weighted average spatial slope values such as represented by the correlation signal 123 shown in FIG. 7, i.e. each correlation class for those two minimum spatial slope values which are located within the regions of the two time limits of the related time window like, for example, the time limits 127a and 127b of the time window 127 shown in FIG. 4 for the spatial slope signal 104 or the associated heart cycle or beat 101. Such two minimum spatial slope values are located in the regions of the two ends or time limits of the related time window. For this investigation, it is required that these two minimum spatial slope values must be located in an environment which contains a determinable number of similarly small spatial slope values. During step 39h there are also determined the moments of time at which the two minimum spatial slope values respectively occur in the starting region and in the end region of the sequence of consecutive weighted average spatial slope values.

The following step 39i of the inventive method starts from the moments of time at which the smallest spatial slope values occur for each sequence of consecutive weighted average spatial slope values or each class and from the displacements or temporal offsets which have been utilized for the individual sequences of consecutive spatial slope values during the correlation operation. On this basis, there is then determined for each individual sequence of consecutive spatial slope values like, for example, the sequence 107 of the consecutive spatial slope values 110 to 118 in FIG. 5, and thus for each time window 127, 128, 129 etc., those moments of time which are associated with the minimum spatial slope values, for example, the minimum spatial slope values 133 and 134 shown in FIG. 4 in time window 127. Provided there are not placed very high requirements regarding the precision at which the position of the starting points and the end points of, for example, the QRS loop or wave 8 in the heart cycle or beat 101 referred to in FIG. 4, the moments of time which have been determined in the manner as described hereinbefore, represent a good approximation to such starting points and end points.

For a more precise determination of the starting points and of the end points of, for example, the QRS loops or waves 8, there is set for each one of the two detected minimum spatial slope values like the minimum spatial slope values 133 and 134 shown in FIG. 4 with respect to the time window 127, a small time interval 135 and 136 and this operation is carried out for each sequence of consecutive spatial slope values like, for example, the sequence 107 of consecutive spatial slope values 110 to 118 shown in FIG. 5. Such a time interval preferably encompasses a predetermined number of m sampling intervals, for example, ten sampling intervals for m=10. This operation is carried out during steps 40 and 41.

During the further steps 42, 43 and 44 there are utilized the measured data or potential values which are associated with predetermined moments of time within the aforementioned small time intervals 135 and 136, for determining the difference, i.e. the spatial distance between respective two measured data or potential values which are associated with different ones of the small time intervals 135 and 136. With respect to FIG. 2, this operation implies that the spatial distances 27a, 27b etc., are determined between the points 11a, 12a, 11b, 12b etc., in the different projections 8a, 8b etc., of the QRS loop or wave 8 onto the different planes defined by the triaxial coordinate system 5. For reasons of better clarity of illustration, the aforementioned points have been shown widely spaced from the aforementioned measured data or potential values or moments of time which are associated with the minimum spatial slope values. The spatial distances between the end points of the vector such as the vector 6 in FIG. 2 in a triaxial coordinate system such as the triaxial coordinate system 5 in FIG. 2, can be computed in accordance with the following known formula:

$$a = \sqrt{(X1 - X2)^2 + (Y1 - Y2)^2 + (Z1 - Z2)^2}$$

wherein the two different measured data or potential values are designated by the index numbers 1 and 2.

The values which are thus obtained for the spatial distances between the measured data or potential values associated with related moments of time in the two small time intervals 135 and 136, are now investigated for the minimum spatial distance. A scanning or sampling time or moment of time is associated with each one of these measured data or potential values. The scanning or sampling moments of time of the two measured data or potential values which have the smallest spatial distance, are now respectively defined as the starting point 20 and the end point 21 of the QRS loop or wave 8 or as the null or zero point 7 of such QRS loop or wave 8. These operations are performed during the steps 45 to 54 in the flow diagram illustrated in FIGS. 3c and 3d.

The method described hereinbefore is particularly well suited in instances in which all data are first detected and evaluated subsequently. However, the method can also be adapted to an immediate continuous or on-line data evaluation which is performed already during the data detection and storage or the data logging operation.

For this purpose, for example, a fixed spatial slope value can be predetermined for the first detected measured signal or for the first heart cycle or beat 101. The first detected spatial slope value which equals this predetermined spatial slope value, yields a scanning or sampling moment of time which is set as the reference time or reference moment of time 24. Starting from this reference time or reference moment of time 24, the starting point and the end point of the QRS loop or wave 8 are determined in the aforedescribed manner.

With respect to the second measured signal or the second heart cycle or beat 102 of the series of measurements, an improved assumption can be made for the reference time or the reference moment of time of the second heart cycle or beat 102 by determining, after the determination of the reference time or reference moment of time 24 of the first heart cycle or beat 101, the maximum spatial slope occurring in the same direction in the second heart cycle or beat 102 and by considering the associated scanning or sampling moment of time as the new reference time or reference moment of time for the second heart cycle or beat 102.

Furthermore, the time duration between the now known reference times or reference moments of time 24 and 28 which are respectively associated with the first and the second heart cycle or beat, see FIG. 1, can be measured and plotted while starting from the starting point and the end point of the second heart cycle or beat 102. In this manner, there are obtained the starting point and the end point of the second heart cycle or beat 102.

In this manner, the determination of the reference time or reference moment of time and, on the basis thereof, the determination of the starting point and of the end point of the QRS loops or waves can be continuously improved. As a result of this procedure there are unobjectionably established for each heart cycle or beat or, generally, for each period of the physiological signal under consideration, the starting point and the end point of the signal or of different signal portions with respect to their occurrence in time as well as with respect to their electric potential which is derived therefrom. It will be recognized that this method is particularly suited for evaluating the detected data by means of a data processing system or by means of a computer.

The method described hereinbefore also offers the possibility of determining the so-called J-point. In the illustration of FIG. 1 the point 21 corresponds to such J-point. For the purpose of determining the J-point the rear small time interval like the small time interval 136 associated with the time window 127 shown in FIG. 4, is investigated for the first-occurring spatial slope value which is below a preset limit. The measured value of the J-point is also associated with the moment of time at which the aforementioned first spatial slope value appears. In healthy human beings, the J-point coincides with the end point of the QRS loop or wave 8.

While there are shown and described present preferred embodiments of the invention, it is to be distinctly understood that the invention is not limited thereto, but may be otherwise variously embodied and practiced within the scope of the following claims.

Accordingly, what I claim is:

1. A method of determining the starting point and the end point of a spatial closed signal pattern in a time sequence of individual ones of such spatial closed signal patterns, each of which is constituted by a series of signals measured at predetermined moments of time, said method comprising the steps of:

determining a predetermined number of spatial slope values for each one of a predetermined number of the spatial closed signal patterns;

selecting a preselected sequence of consecutive spatial slope values for each one of said predetermined number of spatial closed signal patterns;

mutually correlating the preselected sequences of consecutive spatial slope values of said predetermined number of spatial closed signal patterns and classifying said sequences into different correlation classes in accordance with their mutual correlation;

said step of mutually correlating said preselected sequences of consecutive spatial slope values includes mutually correlating said preselected sequences of consecutive spatial slope values at a predetermined temporal offset between individual ones of said preselected sequences of consecutive spatial slope values;

forming a sequence of consecutive weighted average spatial slope values for each correlation class of said mutually correlated sequences of consecutive spatial slope values;

determining a minimum spatial slope value within each end region of each said sequence of consecutive weighted average spatial slope values; and determining by means of each said minimum spatial slope value of each said sequence of consecutive weighted average spatial slope values and said predetermined temporal offset between individual ones of said preselected sequences of consecutive spatial slope values, the minimum spatial slope values of each said preselected sequence of consecutive spatial slope values and thereby the starting points and the end points of each related one of said predetermined number of spatial closed signal patterns.

2. The method as defined in claim 1, further including the steps of:

defining predetermined time intervals about each one of said minimum spatial slope values of each said preselected sequence of consecutive spatial slope values;

selecting the spatial closed signal pattern which is associated with the preselected sequence of consecutive spatial slope values;

determining a preselected number of points on said associated spatial closed signal pattern and which points correspond to points within said predetermined time intervals about each one of said minimum spatial slope values of the preselected sequence of consecutive spatial slope values with which said spatial closed signal pattern is associated;

determining the spatial distance between said preselected number of points on said associated spatial closed signal pattern; and selecting the points associated with the minimum determined spatial distance and setting such points as the starting point and the end point of said associated spatial closed signal pattern.

3. The method as defined in claim 1, wherein:

said step of determining the minimum spatial slope value within each end region of each said sequence of consecutive weighted average spatial slope values entails determining for each said minimum spatial slope value one of a plurality of consecutive similarly small spatial slope values.

4. The method as defined in claim 1, wherein:

said step of determining the minimum spatial slope value within each end region of each said sequence of consecutive weighted average spatial slope values entails determining for each said end region two very small spatial slope values.

5. The method as defined in claim 2, further including the steps of:

receiving a time sequence of signals measured at predetermined sampling intervals; and said step of defining said predetermined time intervals entailing the step of defining predetermined time intervals which comprise a preselected number of said sampling intervals and which are associated with each one of said minimum spatial slope values of each said preselected sequence of consecutive spatial slope values.

6. The method as defined in claim 1, further including the step of:

arranging a predetermined number of electrodes in a predetermined configuration at a predetermined region of the body of a living being under examination and receiving the time sequence of spatial closed signal patterns by means of said electrodes.

7. The method as defined in claim 6, wherein:
said step of arranging said predetermined number of electrodes and receiving said time sequence of spatial closed signal patterns entails receiving the QRS loops of a vector cardiogram curve.

8. The method as defined in claim 1, wherein:
said step of determining said predetermined number of spatial slope values for each one of a predetermined number of spatial closed signal patterns entails filtering said predetermined number of spatial slope values in accordance with a band-pass characteristic.

* * * * *